United States Patent
Ghiasvand et al.

(10) Patent No.: US 10,191,019 B2
(45) Date of Patent: Jan. 29, 2019

(54) VACUUM-ASSISTED IN-NEEDLE CAPPLICARY ADSORPTION TRAP WITH MULTIWALLED POLYANILINE/CARBON NANOTUBE NANOCOMPOSITE SORBENT

(71) Applicants: Alireza Ghiasvand, Khorramabad (IR); Fatemeh Yazdankhah, Khorramabad (IR); Farzaneh Zarghami, Ahvaz (IR)

(72) Inventors: Alireza Ghiasvand, Khorramabad (IR); Fatemeh Yazdankhah, Khorramabad (IR); Farzaneh Zarghami, Ahvaz (IR)

(*) Notice: Subject to any disclaimer, the term of this patent is extended or adjusted under 35 U.S.C. 154(b) by 0 days.

(21) Appl. No.: 15/402,120

(22) Filed: Jan. 9, 2017

(65) Prior Publication Data

US 2017/0184554 A1     Jun. 29, 2017

Related U.S. Application Data

(63) Continuation-in-part of application No. 15/276,400, filed on Sep. 26, 2016, and a continuation-in-part of application No. 15/083,206, filed on Mar. 28, 2016.

(30) Foreign Application Priority Data

Jan. 7, 2016    (IR) .................. 139450140003011441

(51) Int. Cl.
    *B01J 20/281*       (2006.01)
    *G01N 1/14*         (2006.01)
    (Continued)

(52) U.S. Cl.
    CPC .......... *G01N 30/482* (2013.01); *B01J 20/205* (2013.01); *B01J 20/262* (2013.01);
    (Continued)

(58) Field of Classification Search
    CPC .... G01N 30/12; G01N 2030/121; G01N 1/14; G01N 1/22; G01N 1/2214; G01N 1/2294; G01N 30/06; G01N 30/54; G01N 30/482; G01N 2030/009; G01N 2030/025; G01N 2030/027; G01N 2030/062;
    (Continued)

(56) References Cited

U.S. PATENT DOCUMENTS

| | | |
|---|---|---|
| 4,014,797 A | 3/1977 | Raines et al. |
| 5,064,418 A | 11/1991 | Cronin |

(Continued)

OTHER PUBLICATIONS

Non-Final Office Action Issued in U.S. Appl. No. 15/083,206, dated Mar. 22, 2018, 23 pages.

*Primary Examiner* — Manish S Shah
*Assistant Examiner* — Suman K Nath
(74) *Attorney, Agent, or Firm* — NovoTechIP International PLLC

(57) ABSTRACT

A vacuum-assisted in-needle capillary adsorption trap (VA-INCAT) device for sampling and delivering materials to an analytical device is disclosed. A sorbent is multiwall carbon nanotube/polyaniline (PANI/MWCNT) nanocomposite and is coated within an interior space of the needle between the second end and the side aperture to entrap an analyte within a sample. The VA-INCAT device also includes a vacuum device configured to vacuum the vacuum flask to improve the extraction of the analytes vapors from the sample matrix to the sorbent bed.

8 Claims, 3 Drawing Sheets

(51) Int. Cl.
*G01N 30/06* (2006.01)
*B01J 20/26* (2006.01)
*B01J 20/20* (2006.01)
*G01N 30/00* (2006.01)
*G01N 1/22* (2006.01)

(52) U.S. Cl.
CPC ............ *G01N 1/14* (2013.01); *G01N 1/2294* (2013.01); *G01N 30/06* (2013.01); *B01J 2220/46* (2013.01); *B01J 2220/54* (2013.01); *G01N 1/2214* (2013.01); *G01N 2001/2229* (2013.01); *G01N 2030/009* (2013.01); *G01N 2030/062* (2013.01); *G01N 2030/484* (2013.01)

(58) Field of Classification Search
CPC ....... G01N 2030/484; G01N 2030/488; G01N 33/24; G01N 2001/2229
USPC ........... 73/23.35–23.42, 31.07, 61.52–61.61, 73/64.56, 863.12; 210/656–659; 95/82, 95/87, 90–148; 96/101–107, 112, 96/143–146; 422/69, 70, 88, 89
See application file for complete search history.

(56) References Cited

U.S. PATENT DOCUMENTS

| | | |
|---|---|---|
| 7,749,443 B2 | 7/2010 | Land, III |
| 2007/0056360 A1 | 3/2007 | Grant |
| 2009/0308811 A1 | 12/2009 | Tepper |
| 2013/0233054 A1 | 9/2013 | Oliphant et al. |
| 2014/0318274 A1 | 10/2014 | Zimmerman |
| 2015/0233655 A1 | 8/2015 | Ghiasvand |
| 2016/0320271 A1* | 11/2016 | Schueler ............... G01N 1/2226 |
| 2017/0059533 A1* | 3/2017 | Ghiasvand ........... G01N 30/482 |
| 2018/0038777 A1* | 2/2018 | Ghiasvand ........... G01N 1/2214 |

* cited by examiner

VACUUM-ASSISTED IN-NEEDLE CAPPLICARY ADSORPTION TRAP WITH MULTIWALLED POLYANILINE/CARBON NANOTUBE NANOCOMPOSITE SORBENT

CROSS REFERNCE TO RELATED APPLICATION

This application claims the benefit of priority to an Iran Application Serial Number 139450140003011441, filed on Jan. 7, 2016, entitled "A vacuum-assisted in-needle capillary adsorption trap device with polyaniline/carbon nanotube nanocomposite sorbent" and issued as Iran Patent Number 88933. This application is also a continuation-in-part application of U.S. Application Serial Number 15/276,400, entitled: "ELECTROPOLYMERIZATION OF NANOPARTICLES IN-NEEDLE CAPPLICARY ADSORPTION TRAP FOR ANALYZING VOLATILES AND SEMI-VOLATILES IN COMPLICATED MATRICES", filed on Sep. 26, 2016 and U.S. application Ser. No. 15/083,206, entitled: "A COOLING-ASSISTED NEEDLE TRAP DEVICE FOR ANALYZING COMPLEX SOLID SAMPLES USING NANO-SORBENT", filed on Mar. 28, 2016. The entire content of the above-identified applications are incorporated herein by reference.

TECHNICAL FIELD

This application relates generally to a Vacuum-Assisted In-Needle Capillary Adsorption Trap (VA-INCAT) for sampling that can be used to extract analyte from complicated solid samples and deliver the extracted analyte to a gas chromatography (GC) system. More specifically, the application discloses a vacuum system to assist and enhance the extraction of the analyte.

BACKGROUND

Historically, the chief method of analyzing trace volatile chemicals (analytes), was solid-phase micro-extraction (SPME) which employs a fiber to collect the analyte and inject it into a gas chromatograph (GC) or liquid chromatograph (LC). This resulted in the capture and injection of only small quantities of the analytes and thus yielded poor sensitivity. It was discovered that if large quantities of vapor or liquid analyte were drawn through a treated sorbent inside a capillary needle, the components of interest would be more significantly concentrated. The capillary needle was directly injected into GC injection port to desorb the analytes using carrier gas of GC. Additionally, solvents may be used to selectively remove the analyte from the sorbent and a small portion of the solvent containing the analytes injected into the GC or LC.

Moreover, the environmental impact, chemical composition, concentration trends, and health effects of airborne particulate matter have been extensively studied and described in the literature. Current sampling methods involve the use of gravimetric filters or impact devices, and a wide variety of light and laser scattering devices. Many of the analytical methods for determination of chemical composition of airborne particulate matter require either sophisticated equipment and/or use strict sample preparation techniques. The task of sampling and analysis of airborne particulate matter is often complicated by the complexity of particle size, particle interactions, chemical partitioning between gaseous and particulate phase, and interactions with the sampling media. The health effects of inhaled particulate matter are associated with both the size and shape, as well as chemical toxicity. One of the better known groups of analytes from the latter category is polycyclic aromatic hydrocarbons (PAHs).

Amongst pollutants, PAHs have received increased attention in recent years due to their suspected carcinogenic and/or mutagenic nature. PAHs originate in incomplete combustion, and are commonly found in gasoline and diesel motor exhaust, as by-products of open fires, industrial smoke, and cigar tobacco and smoke. Other sources include coal tar, coal tar pitch, wood preserving agents and coatings, mineral oils, and asphalt. Current most widely used sampling method, solid phase extraction (SPE), for PAHs involve the use of high-volume pumps, filters and sorbent cartridges. These methods require extraction from a filter (or sorbent) with an appropriate solvent, followed by subsequent analysis by HPLC with fluorescence or UV detection, or gas chromatography/mass spectrometry (GC/MS). Many of these methods require considerable sampling expertise and sophisticated sampling equipment, long sample collection and sample preparation time, and strict extraction procedures. Thus, there is a growing demand for faster, simpler and cost-effective sampling for analytical methods for airborne PAHs without compromising low detection limits achievable with some of the conventional methods. In addition, these new techniques should be reusable and environmentally friendly.

SUMMARY

The instant application describes a vacuum-assisted in-needle capillary adsorption trap (VA-INCAT) system configured to sample and deliver analyte to an analytical device e.g. GC. Internal surface of an stainless steel needle, may size similarly to GC injection needle, is coated with a sorbent bed and used for extraction of analytes, followed by thermal desorption into the GC injector. All analytes, both freely dissolved in the headspace gas and associated with particulate matter entrained in the sample, may be extracted by the devices.

The VA-INCAT device includes an INCAT, a peristaltic pump, a nano sorbent, a sample matrix, a sample vial, an extraction vial, a two-way valve, a vacuum flask, a silicon septum, an empty needle and a vacuum pump.

The INCAT device includes an stainless steel needle with a first end and a second end. The first end, the syringe tip or the free end, may be configured to engage with a syringe and the second end, the working tip, is configured to be inserted inside an extraction vial. The working tip may include an opening for receiving the sample matrix within the body of the INCAT device.

The extraction vial (a 10 mL SPME sample vial with screw cap and septum) is fixed into the bottom of the vacuum flask (a 250 mL Buchner flask) and attached to a vacuum pump. A two-way valve controls the vacuum. A stainless steel wire opens and closes the sample vial, by passing through the silicon septum of the vacuum flask. The silicon septum may include additional two holes and may seal the vacuum flask. One hole is used for the INCAT device and the other hole is used for a similar, empty needle. The other ends of the needles are attached to the peristaltic pump for circulating the headspace of sample. The solid or liquid sample is placed into the sample vial and its cap is closed. Then, by turning the vacuum pump on, the vacuum flask is vacuumed while the sample vial is closed and remains at atmospheric pressure. After the desired vacuum is reached, the vacuum pump is detached from the vacuum flask. The stainless steel wire opens the sample vial and the pressure gradient causes the analytes to effectively evaporate from the sample matrix. By turning on the peristaltic pump, the sample's headspace is circulated inside the INCAT device and the empty needle for adsorption the analytes vapors on the nanosorbent.

The above general aspect may include one or more of the following features. A sorbent may be packed and placed between the working tip and the side aperture and may be configured to entrap the analyte within the sample received within the interior surface of the needle.

The INCAT device may include gauge 21 stainless-steel needle with a side hole internally coated with polyaniline/multi-wall carbon nanotube composite (PANI/MWCNT), packing nano-composite. The PANI/MWCNT may be synthesized via an electrochemical polymerization/electrophoretic deposition method on the interior wall of the INCAT device. First, aniline may be dissolved in an electrolyte. Then 0.1 g MWCNT may be added to the solution. The solution may then be used as the polymerization solution. Two similar 21G needles may be used as anode and cathodes, respectively. A peristaltic pump may be used to flow the solution. By applying a voltage equal to 1.4 v, the PANI/MWCNT may be formed inside the INCAT device.

The additional details of the present application are set forth in the accompanying drawings and the description below. Once the details of the application are known, additional alternatives and changes will become obvious to one skilled in the art.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

Figure 1:
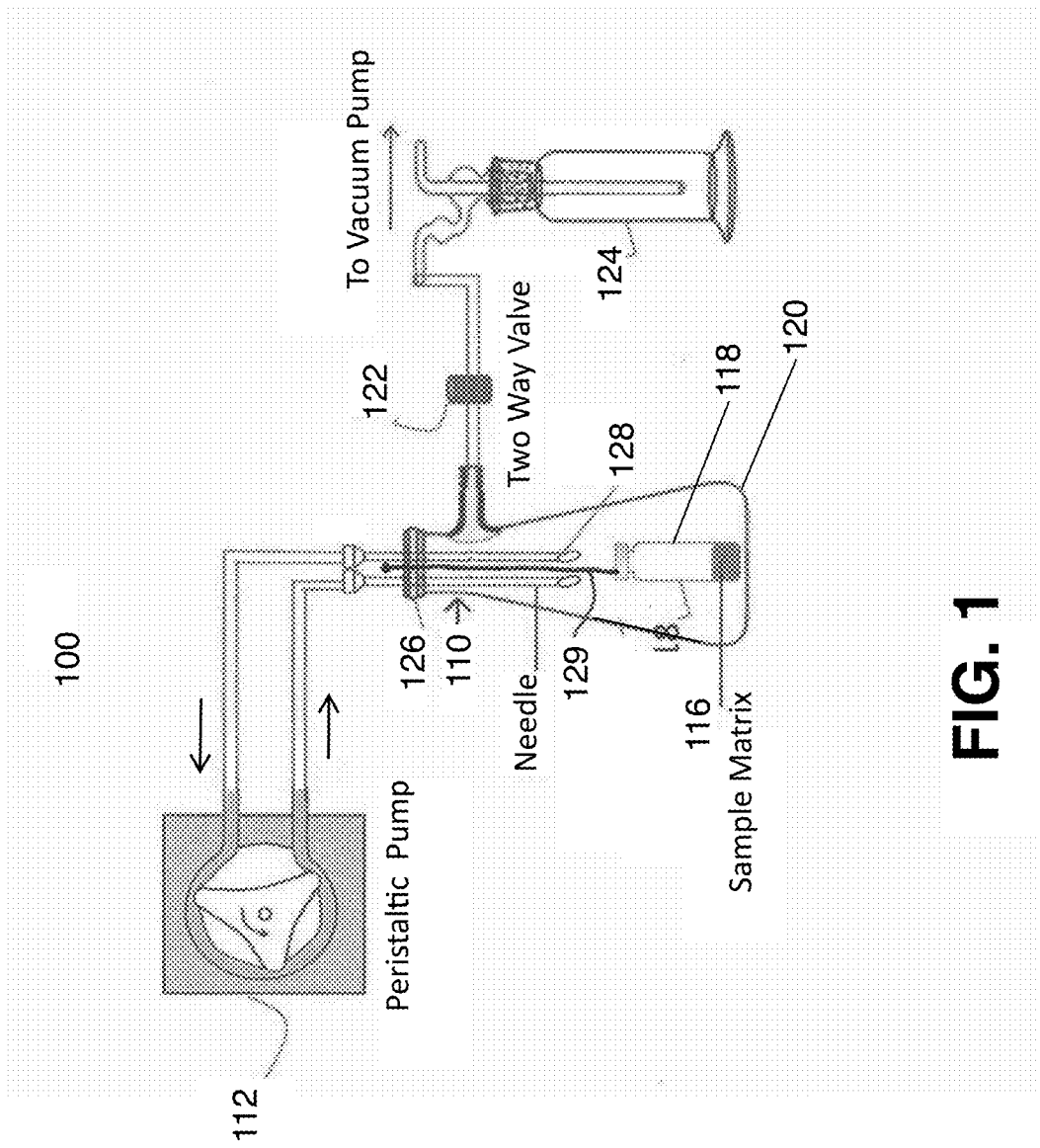
FIG. 1 illustrates a schematic of a vacuum-assisted in-needle capillary adsorption trap (VA-INACT) system according to one implementation of the instant application.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The instant application describes a vacuum-assisted in-needle capillary adsorption trap (VA-INCAT) device configured to sample and deliver analyte to an analytical device e.g. GC device. The GC instrument is a type of automated chromatography (a technique used to separate mixtures of substances) in which the mixture to be analyzed is vaporized and carried by an inert gas through a special column and thence to a detection device for determination. The VA-INCAT device includes, among others, a stainless steel needle and a sorbet bed, coated onto it interior surface of the needle. The stainless steel needle may size similarly to GC injection needles. The sorbent bed may be packed inside the stainless steel needle (called Needle Trap Device, NTD) or may be coated onto the internal surface of the needle (called Inside-Needle Capillary Adsorption Trap, INCAT). The needle along with the sorbent bed may be used for extraction of samples, followed by thermal desorption into GC device. All analytes, both freely dissolved in the headspace gas and those associated with particulate matter entrained in the sample, may be extracted by the VA-INCAT system.

In one implementation, the sorbent is coated onto the internal surface of needle between the working tip and a side hole. For desorption, the needle is inserted into the hot injector GC with a narrow-neck liner, which is individual for SPME experiments. In this stage, the syringe end is sealed against the carrier gas, however, the carrier gas is diverted into the needle through the side hole, subsequently passing through the sorbent, and analytes are thermally desorbed and carried into the GC column. INCAT may be used for either spot (grab) sampling or integrated (time-weighted-average sampling).

For spot sampling a gas tight syringe or gas sampling pump may be connected to the free end of the needle and used to draw a pre-defined sample volume through the needle. The gas concentration is determined by determining the amount adsorbed in INCAT and dividing by the sample volume. For integrated sampling, the syringe tip and side-hole are sealed and the open working tip of the needle is exposed to the sample for an extended period of time. Dynamic sampling includes Grab and TWA. In TWA the gaseous sample is passed through the device for a defined period of time, while the INCAT or NTD is connected to a pump, not sealed. The open working tip of the needle provides a suitable diffusion restriction to provide for analyte uptake rates proportional to sample concentration for several hours. The amount desorbed is thus related to the average sample concentration during the entire exposure time.

As for other gas sampling sorbent tubes, sampling rate and volume should be standardized and minimum breakthrough volume should be determined for the target sample during method development. The INCAT device may be more robust than SPME. The INCAT may have a higher sorbent capacity, which makes it capable of performing exhaustive extraction. Depending on the type of sample and detection system, the INCAT device may be re-used from a few to dozens of times. To date INCAT device has been used primarily for environmental analysis and breath analysis but is amenable to be applied for additional agricultural, pharmacological, biological, biochemical and analytical chemistry applications. Sampling from headspace of water or solid samples by INCAT is a new and challenging topic in this area.

FIG. 1 illustrates a VA-INCAT device 100 in accordance with one implementation of the instant application. The VA-INCAT device 100 may include an INCAT 110, a peristaltic pump 112, a nano sorbent (not shown), a sample matrix 116, a sample vial 118, an vacuum flask 120, a two-way valve 122, a vacuum trap 124, a silicon septum 126, an empty needle 128, a vacuum pump (not shown), and a steel wire 129 to open-close the sample vial's cap.

The INACT device 110 may include a needle having a first end and a second end. The first end, the syringe tip or the free end, may be configured to engage with a syringe or a peristaltic pump and the second end, the working tip, is configured to be inserted inside an vacuum flask 120, through the silicon septum 126. The working tip may include an opening for receiving the sample headspace 116 within the lumen of INCAT device 110. The INACT device 110 may include a sorbent, coated on its interior surface. The sorbent may be placed within the INACT device 110, between the working tip and a side opening. The side opening may be located between the working tip and syringe top of the INACT device 110.

The vacuum flask 120 may be coupled to a vacuum pump (not shown) via vacuum trap 124. The vacuum trap 124 may be used for protecting the vacuum pump. As such, the vacuum trap 124 may be optional component and may be eliminated from the system 100. The vacuum flask 120 may be connected to the vacuum trap 124 via a connection tube. One end of the connection tube may be connected to the top portion of the vacuum flask 120 and another portion of the connection tube may be connected to the top portion of the vacuum trap 124. A two-way valve 122 may be coupled to the connection tube and may control the vacuum.

A extraction (or sample) vial 118 is located inside the vacuum flask 120. In one specific example, the sample vial is 10 ml. The sample vial 118 may house a sample matrix 116. The sample vial 118 may also include a stainless steel wire. The stainless steel wire may be configured to open and close the sample vial 118 cap. A silicon septum 126 with three holes seals the vacuum flask 120. One hole is used for the INCAT device 110 and the other hole is used for a similar, empty needle 128. The third hole may be used for passing through the stainless steel tube wire 129 to open and close the cap of the sample vial 118. The INCAT device 110 and the empty needle 128 may be positioned above 30 mm apparat from each other. The other ends of the needles are attached to the peristaltic pump 112 for circulating the analyte vapors.

By turning the vacuum pump on, the vacuum flask 120 is evacuated while the sample vial 118 is closed and remains at atmospheric pressure. After the desired vacuum is reached, the vacuum pump is detached from the vacuum flask 120. The stainless steel wire opens the sample vial 118 and the pressure gradient causes the analytes to evaporate from the sample matrix 116 placed inside the sample vial 118. The nano sorbent placed inside the INACT device 110 adsorbs the analytes. By turning on the peristaltic pump 112, the analyte vapors circulate inside the INACT device 110 and the empty needle 128 for further adsorption on the nano sorbent 114.

As noted above, the INACT device 110 includes a working tip, a syringe tip, a side hole, and a sorbent bed positioned inside the INACT device 110 between the working end and the side hole. Upon exerting the pressure gradient, the analyte releases from the sample and enters the working end of INACT device 110 where it adsorbs on the nano-sorbent surface. Unlike the conventional methods where some sample preparation step is required to extract the analytes, the sample matrix 116 is placed inside the sample vial 118, without any sample pretreatment and after completeness of the extraction, the INACT device 110 is introduced into a GC injector for sample desorption without further preparation steps. The advantages of such a system are many, e.g., there may be no solvents involved, the total sampling and analysis time may be relatively short, about 15 minutes, and significantly reduced when compared to many existing methods. As such, it can serve as a screening tool, wherever fast analysis is needed. In addition, such a device can also serve as a time-weighted average sampler, where either continuous sampling over long sampling time or a sequence of short sampling events within a required sampling period is used.

The INACT device 110 may include gauge 21 stainless-steel needle, with a side hole, coated internally with PANI/MWCNT nanocomposite sorbent. The PANI/MWCNT nanocomposite was synthesized via an electrochemical polymerization/electrophoretic deposition method on the interior wall of the INCAT device. First, aniline was dissolved in an electrolyte. Then 0.1 g MWCNT was added to the solution. The solution was used as the polymerization solution. Two similar 21G needles were used as anode and cathodes, respectively. A peristaltic pump was used to flow the solution. By applying a voltage equal to 1.4 v, the PANI/MWCNT composite was formed inside of the INCAT device.

Figure 2:
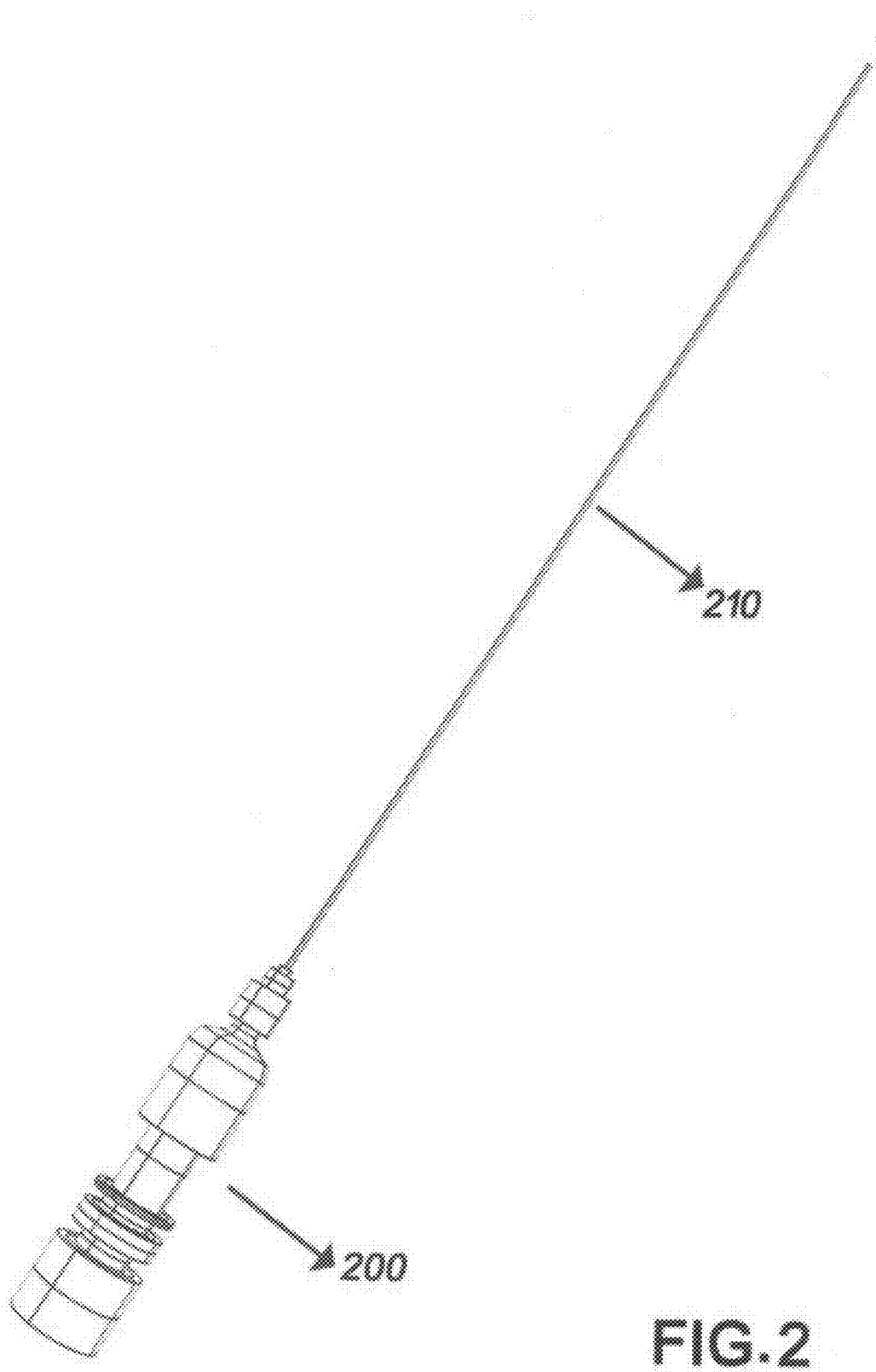
FIG. 2 illustrates an exemplary INACT device according to one implementation of the instant application.

FIG. 2 illustrates an exemplary INACT device 200 in more details. The INACT device 200 includes a working tip 210, a syringe tip, a side hole, and a sorbent thin layer covered inside the INACT device 200 between the working end 210 and the side hole. The working tip of the INCAT device 200 surrounded by the cooling system, which is positioned outside the vacuum flask 120 and on top of the silicon septum 126. Upon heating the sample by the heater below the vacuum flask 120, the analyte releases from the sample and enters the working end of the INACT device 200 where it adsorbs on the nanosorbent surface. The un-adsorbed part of the analyte may be sucked by the peristaltic pump and be returned to the vacuum flask 120 for further extraction. Unlike the conventional methods where some sample preparation step is required to extract the analytes, the sample matrix 116 is placed inside the sample vial 118, without any sample pretreatment and after completeness of the extraction, the INACT device 110 is introduced direct into a GC injector for sample desorption. The advantages of such a system are many, e.g., the extraction trap device may not require sample pretreatment and solvents involved and the total sampling and analysis time may be relatively short and significantly reduced when compared to many existing methods. As such, it can serve as a screening tool, wherever fast analysis is needed. In addition, such a device can also serve as a time-weighted average sampler, where either continuous sampling over long sampling time or a sequence of short sampling events within a required sampling period is used.

Figure 3:
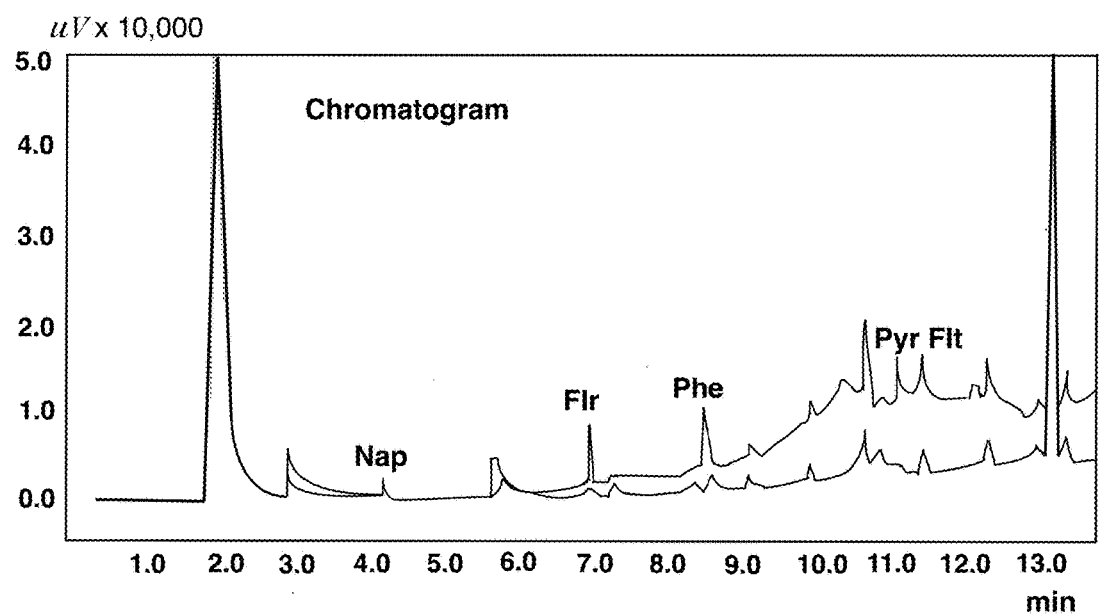
FIG. 3 illustrates a GC-FID chromatogram of the contaminated soils analyte according to one implementation of the instant application.

FIG. 3 shows a GC-FID chromatogram of PAHs extracted from the contaminated soils, which was analyzed by the VA-INCAT setup of the present application. The Limit of Detection (LOD) of 5 PAHs was 0.0001 µg/g and the Relative Standard Deviation (% RSD, n=5) was 6.3%-10.0%.

In one implementation, after extracting the analyte on the sorbent, the INCAT device may be detached from the septum of the VA-INACT system and attach to the injection port of a chromatograph e.g. GC-FID to measure the analyte quantitatively. The free end of the needle may be sealed by a proper silicon septum to avoid the carrier gas from purging.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A vacuum-assisted in-needle capillary adsorption trap (VA-INACT) system comprising:
   a first needle including a first end and a second end and a side aperture positioned between the first end and the second end, and the side aperture being configured to provide access to an interior space of the needle;
   a second needle placed adjacent to the first needle and including a first end and a second end;
   a sorbent coated between the second end and the side aperture within the interior space of the first needle and configured to entrap an analyte attached to a sample placed within a sample vial;
   a vacuum flask including a first opening and a second opening and configured to house the sample vial;
   a first cover configured to cover an opening of the sample vial;
   a second cover configured to cover the first opening of vacuum flask and including three apertures, a first of the three apertures configured to receive the first needle within an interior space of the extraction vial, a second of the three apertures configured to receive the second needle within the interior space of the extraction vial, and a third of the three apertures configured to receive a wire for opening the first cover of the sample vial;
   a peristaltic pump including an inlet and an outlet respectively coupled to the second ends of the first and second needles and configured to circulate the extracted analyte though the first needle and the second needle to improve analyte adsorption on the sorbent inside the first needle; and
   a vacuum device configured to evacuate the interior space of the vacuum flask and improve the efficiency of the extracting the analyte, wherein:
   the vacuum device includes a valve, a vacuum trap and a vacuum pump,
   the vacuum flask is coupled to the vacuum trap via a connection tube,
   the connection tube connect the vacuum trap to the second opening of the vacuum flask,
   the vacuum pump is in communication with the vacuum trap and the vacuum flask and is configured to provide a vacuum within the interior space of the vacuum flask, and
   the valve configured to operate between an open position and a closed position, wherein in the closed position the valve disables the communication between the vacuum pump and the vacuum flask and in the open position the valve enables the communication between the vacuum pump and the vacuum flask.

2. The system of claim 1, wherein the third aperture of the three apertures in the second cover is configured to receive a mechanism for opening the first cover of the sample vial once the interior space of the vacuum flask reaches a vacuum state.

3. The system of claim 2, wherein the second cover is configured to provide an airtight seal for the extraction vial.

4. The system of claim 3, wherein the first and second needles are made of stainless steel.

5. The system of claim 4, wherein the first needle is 21-G in diameter.

6. The system of claim 3, wherein the sorbent is polyaniline/multi-wall carbon nanotube-composite.

7. The system of the claim 6, wherein the sorbent is made by a 2-electrode electrochemical polymerization/electrophoretic deposition technique.

8. The system of the claim 7, wherein the electrolyte is a mixture of multiwall carbon nanotube and aniline in an electrolyte.

* * * * *